(12) United States Patent
Bradley

(10) Patent No.: US 7,174,215 B2
(45) Date of Patent: Feb. 6, 2007

(54) METHOD FOR DETERMINING STIMULATION PARAMETERS

(75) Inventor: Kerry Bradley, Glendale, CA (US)

(73) Assignee: Advanced Bionics Corporation, Sylmar, CA (US)

(*) Notice: Subject to any disclaimer, the term of this patent is extended or adjusted under 35 U.S.C. 154(b) by 436 days.

(21) Appl. No.: 10/728,455

(22) Filed: Dec. 5, 2003

(65) Prior Publication Data

US 2004/0116978 A1 Jun. 17, 2004

Related U.S. Application Data

(60) Provisional application No. 60/431,507, filed on Dec. 6, 2002.

(51) Int. Cl.
*A61N 1/00* (2006.01)

(52) U.S. Cl. ..................................... 607/59

(58) Field of Classification Search ............... 607/28, 607/46–48, 63, 59
See application file for complete search history.

(56) References Cited

U.S. PATENT DOCUMENTS

| 3,646,940 A | 3/1972 | Timm et al. |
| 3,724,467 A | 4/1973 | Avery et al. |
| 4,640,286 A | 2/1987 | Thomson |
| 5,330,515 A | 7/1994 | Rutecki et al. |
| 5,370,672 A | 12/1994 | Fowler et al. |
| 5,443,486 A | 8/1995 | Hrdlicka et al. |
| 5,782,880 A | 7/1998 | Lahtinen et al. |
| 5,893,883 A | 4/1999 | Torgerson et al. |
| 6,381,496 B1 | 4/2002 | Meadows et al. |
| 6,456,879 B1 | 9/2002 | Weinberg |
| 6,615,082 B1 | 9/2003 | Mandell |
| 7,035,690 B2 | 4/2006 | Goetz |
| 2002/0138124 A1 | 9/2002 | Helfer et al. |
| 2003/0093134 A1 | 5/2003 | Bradley |
| 2004/0199216 A1 | 10/2004 | Lee et al. |

FOREIGN PATENT DOCUMENTS

| EP | 1276538 B1 | 1/2006 |
| WO | WO-02/096512 A1 | 12/2002 |

*Primary Examiner*—Scott M. Getzow
(74) *Attorney, Agent, or Firm*—Vista IP Law Group LLP

(57) ABSTRACT

A method is provided for determining optimal stimulus pulsewidth and stimulus amplitude for stimulating nerves with at least one electrode (17). The method comprises: providing a predetermined calibration curve comprising a set of pulsewidth and amplitude values; and delivering sets of pulsewidths and amplitude values which are part of the calibration curve to the at least one electrode (17) to determine at least the optimal pulsewidth. A pulsewidth (70) and an amplitude can be efficiently selected that is efficacious and provides an ample clinical usage range (UR).

19 Claims, 5 Drawing Sheets

METHOD FOR DETERMINING STIMULATION PARAMETERS

The present application claims the benefit of U.S. Provisional Patent Application Ser. No. 60/431,507, filed Dec. 6, 2002, which application is herein incorporated by reference in its entirety.

BACKGROUND OF THE INVENTION

The present invention relates to methods of stimulating nerves. More specifically, the present invention relates to determining and setting stimulation parameters, i.e., stimulus pulsewidth and amplitude, for stimulating nerves with electrodes.

When a stimulus pulse is used to stimulate a nerve fiber, there are primarily two stimulation parameters that determine the "capture" (or depolarization) of nerve fiber. These stimulation parameters are the pulse amplitude and the pulsewidth. It is well known that these parameters have an interplay in stimulating a nerve fiber. The values of stimulus pulsewidths and stimulus amplitudes which just achieve capture of nerve fiber (depolarization) are inversely related and can be plotted as an X-Y curve. The resulting stimulation threshold curve is the well-known "strength-duration" curve for an individual nerve fiber. The term "strength" refers to the stimulus amplitude and the term "duration" refers to the pulsewidth.

Clinically, however, it may not always be feasible to detect depolarization of a single nerve fiber. Rather, in a clinical setting, what can be evaluated is the mass depolarization of a set of nerve fibers that make up a portion of a nerve bundle. Because each nerve fiber within a nerve bundle has its own characteristic "strength-duration" curve, stimulating a nerve bundle exhibits a "massed" or composite strength-duration curve of many nerve fibers firing together. Such a composite curve may be derived by stimulating a nerve bundle and measuring a detectable threshold physiological event resulting from nerve stimulation, which threshold event is used as a surrogate for the threshold "capture" of a few nerve fibers in the nerve bundle. In other words, while actual detection of individual nerve fiber depolarization is not easily observed without special detection equipment, the end effect of a few nerve fibers depolarizing can often be reasonably measured by the physiological response to the nerve depolarization.

For example, when sensory nerves that mediate the masking of pain are stimulated, the proxy measure of nerve stimulation threshold can be the resulting, just noticeable perceived, masking of pain ("the perception threshold") caused by depolarization of some nerve fibers. Other physiological effects of stimulation of nerve fibers may be used as proxies for determining stimulation threshold for other types of applications. For example, when motor nerves are stimulated with a threshold stimulus, a just visible muscle twitch can be used as a visual indicator that some nerves innervating the muscle are being captured.

There are a number of confounding factors in the optimal selection of stimulus pulsewidth and amplitude for nerve stimulation. These factors include inter-patient variability of perception thresholds and maximum tolerable or maximum comfortable thresholds, as well as variability in electrode impedances within a patient and amongst patients.

For nerve stimulation, the usage range ("UR") of stimulation amplitudes for a constantly held pulsewidth can be defined as the difference between the "maximum comfortable threshold" and the "perception threshold." "Maximum comfortable threshold" is a stimulus level (pulsewidth, amplitude) where beyond that level a patient perceives discomfort or even pain. The "perception threshold" is that stimulus level (pulsewidth, amplitude) where the patient just notices a physiological effect. For example, in cochlear application, in may be a perception of sound. In spinal cord application, it may be a tingling sensation. When narrower pulsewidths are used, the UR of stimulation amplitudes shifts and increases. The UR is expanded because narrower pulsewidths must be compensated by using larger stimulus amplitudes and, hence, each discrete step of programming amplitude provides lesser effect.

Most commercial stimulation systems provide discrete programmable steps of stimulation amplitudes as well as steps of pulsewidths. If a large pulsewidth, e.g., greater than 200 microseconds is selected, the discrete amplitude steps of a stimulator may provide too great an effect between one amplitude step and the next step. Thus, a pulsewidth should be chosen to permit the use of programmable amplitude steps which can finely control the delivery of stimulus energy. This control is achieved when the UR is large, such that each discrete, programmable amplitude step provides a significant, measured increase in stimulation to target nerve fibers and there are a reasonable number of steps between perception and maximum comfortable thresholds.

A related concern is that one cannot simply choose the minimum duration pulsewidth merely to achieve the largest UR. In practice, a stimulator system does not have an infinite compliance voltage. This system compliance voltage limits the absolute stimulus amplitude that can be delivered through the electrodes. High electrode impedance may accentuate this compliance voltage limiting effect. Using a very narrow pulsewidth requires a large compensating stimulus amplitude to capture a target nerve fiber. Such a required stimulus amplitude, however, can exceed the maximum deliverable amplitude of a stimulator which is determined by the system compliance voltage. Thus, in practice, selecting a pulsewidth which is too narrow will prevent the capture of a nerve regardless of the size of the stimulus amplitude chosen.

Sometimes a fixed pulsewidth, such as 210 microseconds, is chosen based on past experience. Using a fixed, relatively large, nominal pulsewidth, such as 210 microseconds, also does not provide optimal stimulation because electrode positions relative to the target nerve fibers can vary widely between patients and within a patient. If such a fixed pulsewidth is used, it may be difficult to differentiate the perception threshold and maximum comfortable threshold. The UR may be too small which can make fine stimulation control difficult. In sum, because there is wide variability between patients and electrode placement/configuration, there is no single pulsewidth value that suffices for every occasion.

To determine the optimum stimulus, many random, stimulus parameter sets (pulsewidth, amplitude) may be delivered through the electrode and the result of each stimulus may be evaluated until a good parameter set is found. However, such a random method can be inordinately time-consuming and taxing to a patient as the number of possible combinations is large.

One example application where an optimal stimulus pulsewidth and amplitude must be determined is in spinal cord stimulation (SCS). SCS systems typically include an Implantable Pulse Generator (IPG) coupled to an array of electrode contacts at or near the distal end of a lead. The IPG generates electrical pulses that are delivered to neural tissue, e.g., the dorsal column fibers within the spinal cord, through the contacts of the electrode array. The electrode contacts can be implanted proximal to the dura mater of the spinal cord. Individual electrode contacts, which may be loosely referred to as "electrodes", can be arranged in a desired pattern on a lead in order to create an electrode array. Individual conductor wires or leads can connect with each electrode contact in the array. The lead may exit the spinal column and attach to the IPG, either directly or through one or more lead extensions.

In an SCS system for treating chronic pain, the electrical stimulus pulses delivered by the system typically have the effect of producing a tingling sensation known as a paresthesia. The paresthesia helps block or at least masks the chronic pain felt by a patient. The stimulus amplitude and stimulus pulsewidth affect the intensity and location of the paresthesia felt by the patient. In general, it is desirable to have the stimulus amplitude and pulsewidth comfortably set to a level which produces paresthesia to block pain but not above a level that may actually result in discomfort or pain apart from the native pain. Moreover, the stimulus amplitude and pulsewidth should be set to a level lower than that which can recruit reflex motor nerves that can cause involuntary muscle contractions.

SCS and other stimulation systems are well accepted for treating chronic pain. An implantable electronic stimulator is disclosed, for example, in U.S. Pat. No. 3,646,940 that provides timed, sequenced electrical impulses to a plurality of electrodes, which patent is herein incorporated by reference. As another example, U.S. Pat. No. 3,724,467, teaches an electrode implant for neurostimulation of the spinal cord, which patent is herein incorporated by reference. A relatively thin and flexible strip of biocompatible material is provided as a carrier on which a plurality of electrodes are formed. The electrodes are connected by a conductor, e.g., a lead body, to an RF receiver, which is also implanted, and which is controlled by an external controller.

Accordingly, what is needed is a method for efficiently selecting optimal stimulus pulsewidth and amplitude, particularly for the SCS application, which provides the best overall UR and stimulation efficacy for a given patient and electrode configuration.

SUMMARY OF THE INVENTION

The present invention addresses the above and other needs by providing a method for efficiently determining the stimulus pulsewidth and amplitude using a predetermined calibration curve that provides sets (pulsewidth, amplitude) of parameters, that may be used as starting point for determining the optimal stimulus pulsewidth and amplitude. The calibration curve used may be pre-adjusted for a number of variable factors, e.g., type of electrode array, placement of the electrode in a particular location of the spinal cord such as the thoracic region or the lumbar region.

In one embodiment of the present invention, there is provided a method of determining optimal stimulus pulsewidth, P1, and maximum comfortable threshold amplitude, A2, for stimulating nerve with at least one electrode, the method comprising: (a) providing a predetermined calibration curve defined by sets of paired parameter values (pulsewidth, amplitude); (b) determining an optimal pulsewidth value, P1, by presenting sets of paired parameter values (pulsewidth, amplitude) that are part of the calibration curve, until a threshold stimulus parameter pair (P1, A1) is found which elicits a threshold or a just noticeable response in a patient; and (c) determining a maximum comfortable threshold amplitude value, A2, by holding constant the pulsewidth, P1, found in the preceding step.

In another embodiment of the present invention, there is provided a method of determining optimal stimulus pulsewidth and amplitude for stimulating nerves with at least one electrode. The method comprises: (a) providing a predetermined calibration curve comprising a set of pulsewidth and amplitude values; and (b) selecting a stimulus pulsewidth and an amplitude which provides a maximum comfortable threshold by delivering stimuli to the at least one electrode, wherein the stimuli is chosen from pulsewidth and amplitude parameter pairs which are part of the calibration curve.

BRIEF DESCRIPTION OF THE DRAWINGS

The above and other aspects, features and advantages of the present invention will be more apparent from the following more particular description thereof, presented in conjunction with the following drawings.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention provides a method for quickly determining the optimal pulsewidth and amplitude parameters of a stimulus pulse. These stimulus parameters are then used thereafter by the stimulation system to provide therapy, e.g., to treat chronic pain with the found stimulus pulsewidth and amplitude. One embodiment of the invention selects a stimulus pulsewidth and amplitude that maximizes the UR of the stimulator, while staying within the bounds of the maximum system compliance voltage. While the present invention, as discussed herein, applies particularly to spinal cord stimulation for masking pain (paresthesia), the method of the present invention may be used equally in other medical applications in which electrodes are used to stimulate nerves.

Before discussing the present method for determining the optimal stimulus pulsewidth and stimulus amplitude, it is instructive to understand the components of a typical SCS system.

Figure 1:
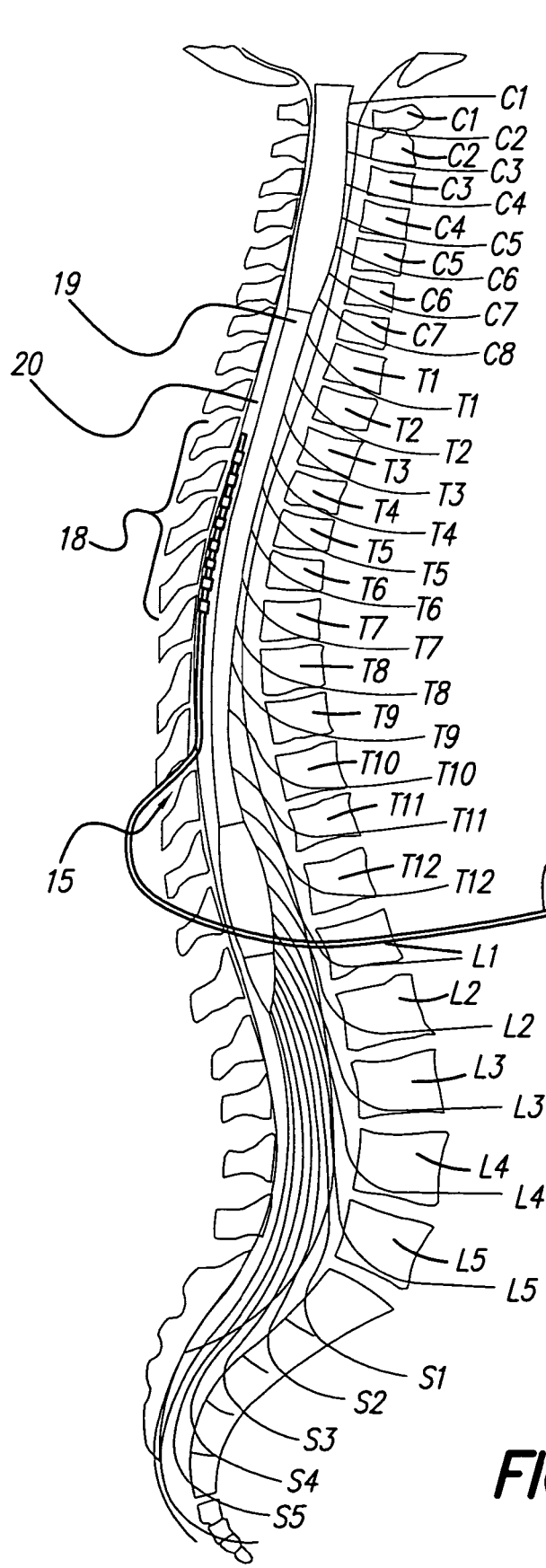
FIG. 1 shows a representative, conventional, neurostimulation system that may be used for many different medical treatment applications.
Figure 1:
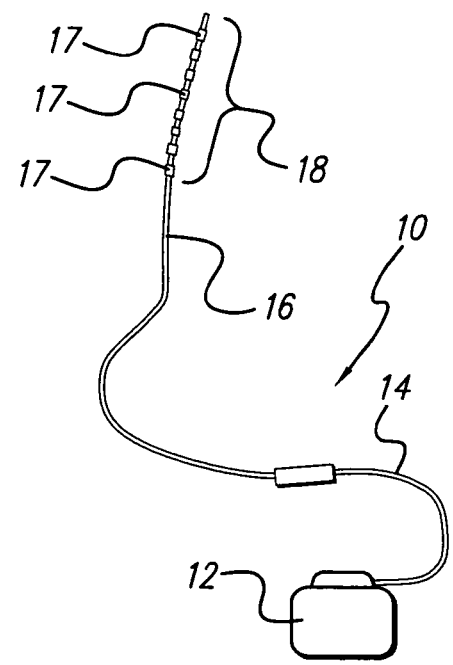
Figure 2:
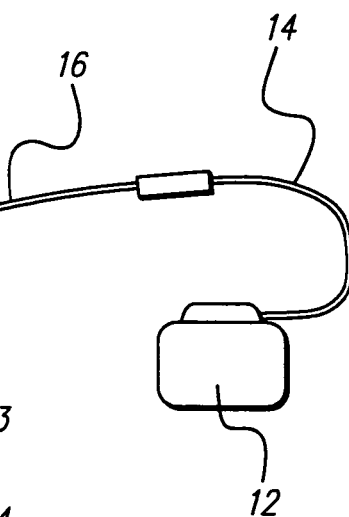
FIG. 2 shows the stimulation system of FIG. 1 being used as a spinal cord stimulation (SCS) system, with an in-line electrode array inserted alongside the spinal cord in the epidural space, in close proximity to the dura mater.

FIG. 1 and FIG. 2 show a representative neural stimulation system. FIG. 2 shows the stimulation system 10 being used as a spinal cord stimulator (SCS) system. In such configuration, the lead 16 and, more particularly, the electrode array 18 is implanted in the epidural space 20 of a patient to be in close proximity to the spinal cord 19.

The system 10 typically comprises an implantable pulse generator (IPG) 12, an optional lead extension 14, an electrode lead 16, having an electrode array 18. The electrode array 18 includes a plurality of electrode contacts 17 (also referred loosely as "electrodes"). The electrode contacts 17 are arranged, for example, in an in-line array 18 near the distal end of the lead 16. Other electrode array configurations may also be used. The IPG 12 generates stimulation current pulses that are applied to selected ones of electrodes 17 within the electrode array 18.

A proximal end of the lead extension 14 can be removably connected to the IPG 12, and a distal end of the lead extension 14 can be removably connected to a proximal end of the electrode lead 16. The electrode array 18 is formed on a distal end of the electrode lead 16. The in-series combination of the lead extension 14 and electrode lead 16 carry the stimulation current from the IPG 12 to electrodes of the electrode array 18. The lead extension 14 need not always be used with the neural stimulation system 10, but may be used when the physical distance between the IPG 12 and the electrode array 18 requires its use. Because of the lack of space near the lead exit point 15 where the electrode lead 16 exits the spinal column, the IPG 12 is generally implanted in the abdomen or above the buttocks. The lead extension 14 facilitates locating the IPG 12 away from the lead exit point 15.

A more complete description of an SCS system may be found in U.S. Pat. No. 6,516,227, which patent is incorporated herein by reference in its entirety.

Figure 3:
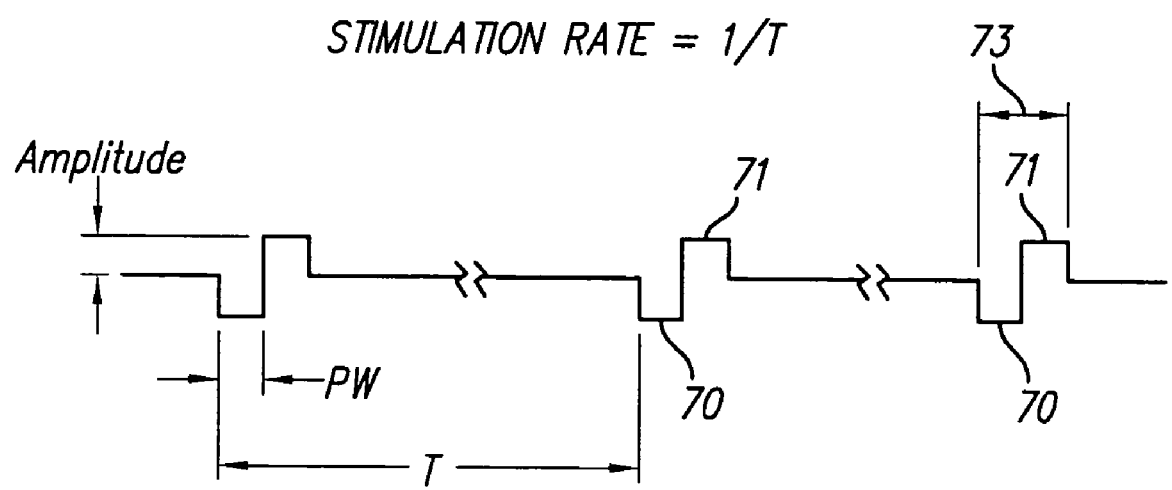
FIG. 3 shows a train of biphasic stimulus pulses that may be delivered by typical neurostimulators such as for the spinal cord stimulation application.

FIG. 3 shows a diagram of a typical stimulus train of biphasic pulses 73. The waveform shown defines stimulation rate (1/T), stimulus pulsewidth (PW) and stimulus pulse amplitude as those terms are commonly used in connection with a neurostimulator device, such as a spinal cord stimulator (SCS), a cochlear implant, a deep brain stimulator (DBS) or other neural stimulator. All such systems commonly generate biphasic pulses of the type shown in FIG. 1 in order to produce a desired therapeutic effect.

A "biphasic" pulse 73 generally consists of two pulses: a first pulse 70 of one polarity (usually negative) having a specified magnitude, followed immediately or after a very short delay, by a second pulse 71 of the opposite polarity having the same total charge, which charge is the product of stimulus current multiplied by the duration of each pulse or phase. It is believed that "charge balancing" can prevent tissue damage at the site of stimulation and prevent electrode corrosion. Generally, it is the first, negative polarity pulse 70, that stimulates the nerve, although it is possible to achieve stimulation, albeit with much less efficiency, with a first, positive polarity stimulus pulse.

The present invention employs a predetermined set of parameter (pulsewidth, amplitude) pairs to quickly determine at least the optimal pulsewidth and then, from there, the optimal amplitude. In one embodiment of the invention, the method for determining the optimal pulsewidth and amplitude comprises: (a) determining the pulsewidth by using one or more parameter pairs (pulsewidth, amplitude) included in the predetermined calibration curve to determine the optimal pulsewidth; and (b) while keeping the identified pulsewidth found in step (a) constant, determining the maximum comfortable stimulus amplitude. This also provides the UR. Determining the final, therapeutic amplitude may require further presentation of stimulus amplitudes to the patient and determining the optimal amplitude. A calculated estimation of the maximum comfortable threshold amplitude may also be obtained based on some multiplicative factor of the selected amplitude used in step (a). The method of the present invention therefore provides the optimal pulsewidth and amplitude for stimulation efficacy, while achieving a reasonable UR.

To understand the rationale for the present invention, it is necessary to understand the relationship between the two stimulus parameters: pulsewidth and amplitude when stimulating an excitable tissue such as a nerve fiber.

Figure 4:
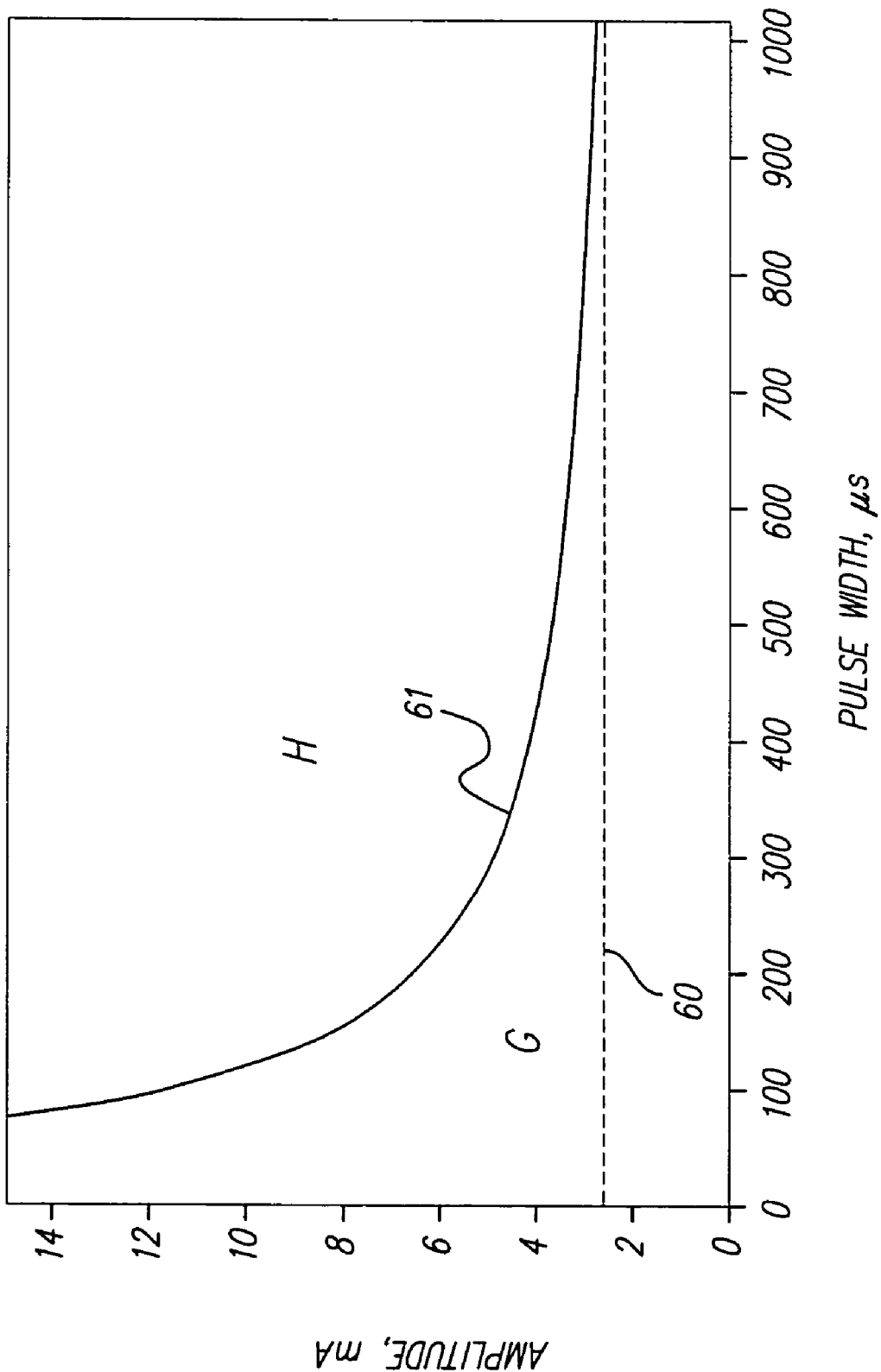
FIG. 4 shows an illustration of one embodiment of a strength-duration curve of a single nerve fiber, in which a threshold curve is plotted with respect to stimulus pulsewidth versus amplitude.

FIG. 4 shows a strength-duration curve of a single nerve fiber showing the inverse relationship between stimulus pulsewidth and stimulus amplitude. The curve indicates the minimum values of stimulus parameter pairs (pulsewidth, amplitude) necessary to "capture" (stimulate) a nerve fiber. The curve depends on many factors such as what type of electrode is used, how closely the electrode is placed to the nerve fiber, what type of nerve fiber is being stimulated, among others. What is important is that all parameter sets (pulsewidth, amplitude) located on one side (G) of curve 61 does not elicit nerve capture, while all parameter sets (pulsewidth, amplitude) located on the other side (H) of the curve 61 provides capture of the target nerve.

The set of stimulus parameters (pulsewidth, amplitude) defining the actual strength-duration curve 61 are all "threshold" stimulation parameters, i.e., that just capture the target nerve fiber. A feature of the strength-duration curve 61 is that there is a minimum current or voltage amplitude, termed the "rheobase", that is required to elicit any nerve stimulation. The rheobase amplitude is signified by the dashed line 60. If the amplitude does not meet or exceed this rheobase value, no nerve capture can occur regardless of the chosen pulsewidth. Similarly there is a minimum pulsewidth value that is required to elicit any nerve stimulation. The strength-duration curve suggests a relationship between pulsewidth and amplitude in which, to some degree, a smaller pulsewidth may be compensated by using a larger amplitude and conversely, a smaller amplitude may be compensated by using a larger pulsewidth to achieve capture of a target nerve.

The Y axis represents the stimulus amplitude and is shown in milliamperes. While the Y axis indicates a constant current stimulus is used in the particular example, it is also be possible to depict a strength-duration curve wherein the stimulus amplitude is constant voltage amplitude. As used herein, "stimulus amplitude", will include either constant current amplitude or constant voltage amplitude embodiments.

Figure 5:
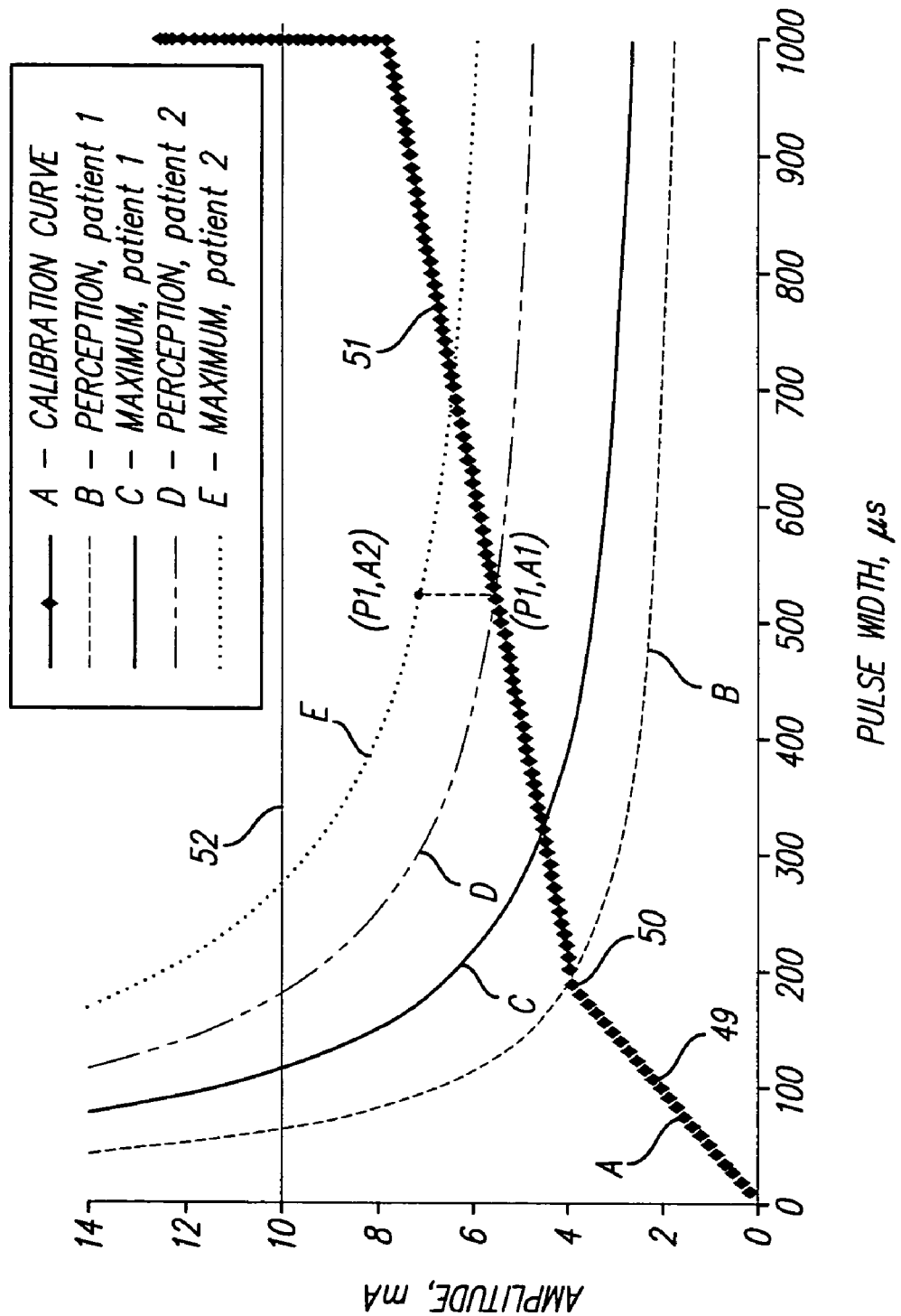
FIG. 5 shows, in accordance with the present invention, a "calibration curve" (curve A) specifying the combinations of possible stimulus pulsewidths and amplitudes that can be programmed, which calibration curve is superimposed over strength-duration curves of two patients, each patient having one curve representing the just noticeable perception threshold ("perception threshold") and one curve representing the maximum comfortable threshold ("comfortable threshold")

FIG. 5 shows, in accordance with the present invention, a predetermined calibration curve A defining a set of stimulus parameter pairs (pulsewidths, amplitudes) that may be employed to find a suitable pulsewidth. As shown, curve A is only one example of a "calibration curve" that may be used, in this case consisting of a set of stimulus parameters (pulsewidth, amplitude) that define a quasi-logarithmic shape. The calibration curve A represents an empirically derived curve chosen to obtain a large UR based on a typical stimulator circuit and physiological limitations.

The X-axis indicates, in this particular example, that the maximum programmable stimulus pulsewidth is 1000 microseconds. The maximum programmable stimulus current amplitude is determined by the particular software (and in some cases hardware) employed and is represented on the Y-axis as 10 milliamperes.

The calibration curve A begins at 0 stimulus amplitude and 0 stimulus pulsewidth. Between pulsewidths of 0 and 200 microseconds which is the first segment 49 of the calibration curve A, it preferably increases at a ratio that is about or slightly greater than the "unity" slope, wherein the "unity" slope is defined as the full-scale available range of amplitude (or largest amplitude) versus the full-scale range of available pulsewidth (or largest pulsewidth). At about a 200 microsecond pulsewidth, there is an elbow 50 in the curve A which signifies the transition to the second portion 51 of the calibration curve A. The elbow 50 shown is at about 200 microsecond pulsewidth which is chosen empirically based on typically obtained strength-duration curves of patients. As the pulsewidth increases beyond 200 microseconds, past the elbow 50, the slope of the calibration curve A is less steep. When the calibration curve reaches the maximum programmable pulsewidth, depicted here as 1000 microseconds, the curve specifies that only the amplitude can be increased, not pulsewidth. This predetermined calibration curve is designed to preferentially select lower pulsewidth values so that a greater UR can be obtained.

It is emphasized that the elbow 50 shown at 200 microseconds in FIG. 5 can occur at another pulsewidth value. Preferably, the elbow will occur somewhere between pulsewidth values of between about 100 to 300 microseconds. Alternatively, a calibration curve having no elbow can be used. What is important is that the calibration curve selected can provide stimulus pulsewidth values that encompass both the typical, clinically obtained perception thresholds and maximum thresholds. At the same time, the calibration curve must be bound somewhere between 0 amplitude and maximum system programmable amplitude represented by the horizontal line 52 at 10 milliamperes. Thus, if the maximum programmable amplitude 52 is decreased, for example, from 10 mA to 7 mA, the calibration curve must be adjusted by decreasing (flattening) the slope of the first part of the calibration curve, the slope of the second part of the calibration curve or the slopes of both parts of the calibration curve A.

As shown in FIG. 5, curves B, C, D and E are various types of strength-duration curves. Curves B and C are for patient number 1 and curves D and E are for patient number 2. Curves B (patient 1) and D (patient 2) represent perception threshold strength-duration curves. Curves B and D are similar to traditional strength-duration curves in that perception threshold may correspond to the stimulus level at which a few nerve fibers are captured. This stimulus level (pulsewidth, amplitude) may be only slightly greater than the stimulus level required to capture a single nerve fiber, which a conventional strength-duration curve is based upon.

Curves C (patient 1) and E (patient 2) represent maximum comfortable threshold strength-duration curves, which are psychophysical responses to a stimulus and therefore are not equivalent to the conventional strength-duration curve for a nerve. Curves C and E define thresholds, which beyond those stimulus levels, a patient experiences discomfort. Curves C and E may represent the recruitment or capture of many nerve fibers at once, and therefore represent "massed" nerve responses. For example, in the SCS application, rather than producing paresthesia, a stimulus exceeding the maximum comfortable threshold may be uncomfortable or even painful of its own accord. Generally, for the best therapeutic effect, the chosen pulsewidth and stimulus amplitude should be below the maximum comfortable threshold curve to provide recruitment of most, if not all, of the sensory nerve fibers in a nerve bundle.

As illustrated in FIG. 5 with two patients, the strength-duration curves can differ widely among individuals. This is due to many factors: different inter-patient and intra-patient distances of an electrode from the target spinal cord nerves, arising from different spinal nerve anatomies; different patient pathologies; different electrode/lead designs and configurations; and different psychophysical definitions of paresthesia perception and maximum comfortable sensory perception. These variable factors translate to differing strength-duration curves for the perception and the maximum comfortable thresholds.

For patient 1, the calibration curve A intersects the perception strength-duration curve B at approximately 4 mA (stimulus current amplitude) and 200 microsecond (stimulus pulsewidth). Assuming that subsequently measured perception thresholds are around 4 mA, the UR for this patient is approximately 2 mA, wherein UR is the difference in amplitude between maximum comfortable threshold and the perception threshold (at a fixed pulsewidth). With the stimulator maximum output limit of 10 mA, there is still about a 4 milliampere margin above the maximum comfortable threshold level for patient 1. Such a margin is desirable since stimulation threshold can change as much as 30% post-implant because of such factors as changes in electrode position in the body resulting from normal patient movement.

Similar results are obtained for patient 2. The calibration curve A intersects the perception threshold strength-duration curve D at approximately 5.5 mA stimulus amplitude and 520 microsecond stimulus pulsewidth. This yields a UR of approximately 1.5 mA. If the calibration curve A had a higher slope in this region, the intersection point might have yielded a lower pulsewidth, for example, a 330 microsecond pulsewidth at 6.8 mA. However, the maximum comfortable threshold value at this pulsewidth would have been approximately 8.9 mA. In that case, there is less of a margin between the maximum comfortable threshold value of 8.9 mA and the stimulator maximum deliverable amplitude of 10 mA. The headroom is only about 1.1 mA, which may be insufficient to deal with stimulation threshold changes post-implant.

The predetermined calibration curve A therefore may take into account the maximum compliance voltage of the stimulator system. The stimulator compliance voltage is an important factor, as it interacts with the impedance of the electrode/lead system. If the impedance of the electrode/lead system is too high, the maximum stimulation amplitude that can be generated by the stimulator may be constrained to a value which is actually lower than the labeled stimulator programmable value. For example, if the impedance of an electrode configuration is 2 KΩ and the system compliance voltage is 15 volts, then the maximum stimulus amplitude is 15 volts/2 KΩ=7.5 mA, which value is lower than the 10 mA example in FIG. 5. Thus, the quasi-logarithmic shape of the calibration curve is a compromise, taking into account the stimulator output limits and physiological parameters for individual patients.

Figure 6:
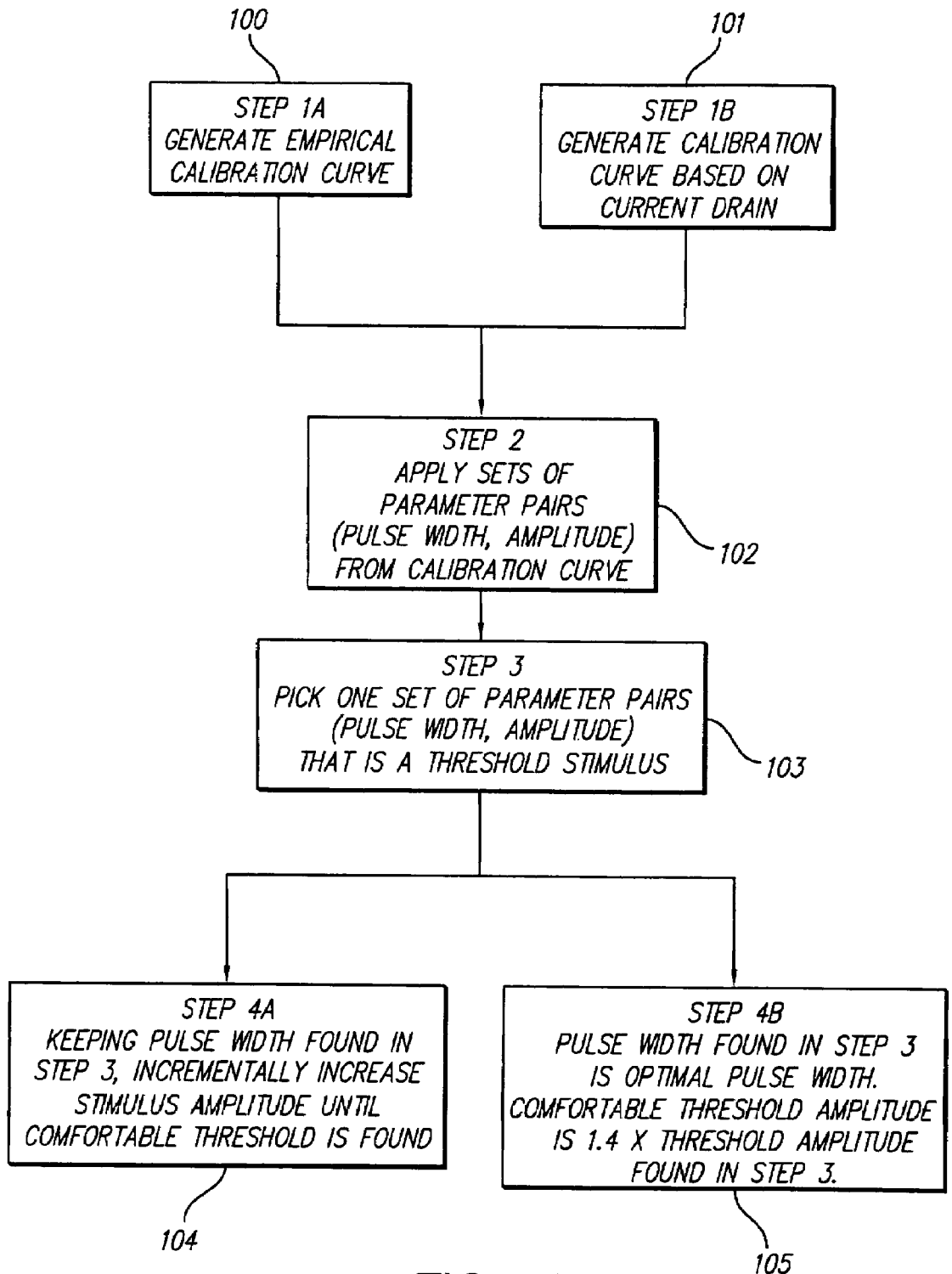
FIG. 6 shows a flowchart illustrating the steps that may be used in accordance with the present invention.

FIG. 6 provides a flowchart illustrating the steps that may be used, in accordance with the present invention to find the optimal, therapeutic, stimulus parameters (pulsewidth, amplitude) as well as the UR.

As a preliminary matter, one embodiment of the present method for determining the optimal stimulus parameter pair (pulsewidth, amplitude) uses a first electrode configuration having the highest impedance among the various possible electrode configurations. Choosing the highest electrode impedance ensures that the choice of pulsewidth and amplitude will be within the bounds of the maximum stimulator compliance voltage for all available electrode configurations (impedances).

Step 1A, shown as the box 100, indicates predetermining a calibration curve that will be used later in order to determine the optimal stimulus pulsewidth and amplitude. The generation of this calibration curve is important for providing an organized method for determining the optimal pulsewidth without employing a time-consuming, random method for testing many combinations of parameter (pulsewidth, amplitude) pairs.

By the use of term "optimal", e.g., optimal pulsewidth or optimal stimulus, optimal means, herein, some value that takes into account such factors as the UR, stimulator compliance and maximum programmable stimulation amplitude. Therefore, there is not necessarily just a single optimum stimulus but more likely an "optimal" range of stimulus parameters or stimulus values within a UR, which this invention seeks to find quickly.

To compensate for the effect of high lead impedance, the predetermination of the calibration curve in Step 100 can be based partly on the measured impedance of the electrode/lead system. Depending on the impedance of the system, the calibration curve can be adjusted downward, such that a larger pulsewidth is initially chosen. This downward shifting of the calibration curve, e.g., the curve A of FIG. 5, ensures that there is sufficient "headroom" so that the programmed stimulation amplitudes are actually delivered.

Optionally, as shown in Step 1B, box 101, the calibration curve can be individually modified for each patient based, instead, upon the calculated current drain of the system using a programmer that is capable of measuring lead/electrode impedance and calculating circuit costs that trade off amplitude size against pulsewidth size. A stored look-up database during the present or previous follow-up can be used to help determine a particular calibration curve to use which can conserve system power.

In an implantable stimulator system, there is always some "overhead" power consumption associated with providing stimulation. This overhead consumption includes background quiescent current drain required for keeping amplifiers and transistors biased, capacitor power losses from running clock signals, etc., as well as current drain in running voltage doublers and triplers, and running switching regulators that supply voltages to the electrodes.

Since every stimulator system differs in electrical design, some stimulators may deliver incremental pulsewidths more efficiently than amplitude (mean current or voltage) increments for the same amount of delivered stimulation charge. The power drain may be quantified as follows:

$$P_{drain} = \{(I_{stim} * Pulsewidth_{stim} * Rate_{stim})^2 * Z_{combination}\} + P_{sys}$$

where $I_{stim}$ (stimulus amplitude), $Pulsewidth_{stim}$, $Rate_{stim}$ (in pulses per second) are all parameters related to the stimulator outputs. $Z_{combination}$ is the resistive impedance for the electrode combination in use and $P_{sys}$ is the overhead power consumption. In the present invention, for a given stimulator system, if $P_{sys}$ has a greater $\Delta P_{sys}/\Delta I_{stim}$ than $\Delta P_{sys}/\Delta Pulsewidth_{stim}$, then the calibration function may be changed to prefer, for the sake of efficiency, changes in stimulation pulsewidth, rather than amplitude. This would be manifested as a "flattening" of the calibration curve A shown in FIG. 5.

It is noted that Step 1A, box 100, and Step 1B are not mutually exclusive. That is, they may be combined into one step or practiced separately. After Step 1A, box 100, or Step 1B, box 101, a predetermined calibration curve will be generated. Such a predetermined calibration curve may be like curve A illustrated in FIG. 5, having an elbow 50. Or it may be another type of calibration curve, having no elbow. An important aspect of the invention is that some type of predetermined calibration curve is employed during the process of finding the optimal stimulus parameters in order to reduce the number of possible parameter pairs (pulsewidth, amplitude) that must be tested on a patient.

With the predetermined calibration generated, the sets of stimulus defined by the parameter pairs (pulsewidth, amplitude) of the calibration curve are applied systematically through an electrode. For example, the smallest available stimulus having the smallest pulsewidth and amplitude may be applied and incrementally increased, in accordance with Step 2, indicated as box 102. Step 3, box 103, indicates that a threshold stimulus is to be determined. This threshold stimulus is defined by a pulsewidth, P1, and amplitude, A1, and represents one point on the calibration curve.

After Step 3, box 103, there are at least two possible options, Steps 4A and 4B. Both options determine the optimal stimulus amplitude, A2. The optimal pulsewidth, P1, has already been found in Step 3. In Step 4A, box 104, the pulsewidth, P1, is kept constant, and the stimulus amplitude is increased beginning at A1, for example, in discrete increments until the amplitude reaches the maximum comfortable threshold amplitude, A2. The UR, spanning A1 to A2, is therefore found. After A2 is found, the therapeutic stimulus amplitude A3 may be set equal to amplitude A2 or A3 may be set to another value that is lower than A2.

Step 4B, box 105, indicates a faster although less accurate option for determining the comfortable threshold amplitude A2. This method circumvents presentation of any further stimulus to the patient and merely sets A2 as A1 times a multiplicative factor 1.4. Thus, instead of varying the stimulus amplitude after finding the pulsewidth, P1, and thereby taking additional programming time, the maximum comfortable threshold amplitude is simply estimated from the obtained perception threshold amplitude, A1, (for a given pulsewidth). Generally, once the perception threshold pulsewidth, P1, and amplitude, A1, are determined, the estimated, maximum comfortable amplitude, A2, can be quickly estimated by multiplying the perception threshold amplitude, A1, by a factor of 1.4. This 1.4 factor, known as the "Threshold Ratio" is an empirically derived value which has been clinically validated. If the calculated, maximum comfortable amplitude value exceeds the maximum programmable amplitude of the system or exceeds the available system compliance voltage, a different calibration curve should be used, such as one having increased pulsewidths for a given amplitude. The effect of making the pulsewidth larger results in a "flatter" calibration curve and provides added head room.

After the comfortable threshold amplitude (P1, A2) is found, including the UR, spanning amplitude levels A1 to A2, as provided in either Step 4A or 4B, a stimulus with therapeutic parameter pair (P1, A3) can be found. For example, A3 may be set equal to A2 or A3 may be set lower than A2. A3 is the therapeutic amplitude which can be applied during a therapy, e.g., for SCS application. For a visual example of the usage range, FIG. 5 shows, for patient number 2, the usage range that can be found using the present invention. In the example, the threshold stimulus is (P1, A1) and the maximum comfortable threshold stimulus is (P1, A2). The UR is determined by the range of amplitudes between A1 and A2 between the Curve D (threshold perception curve) and Curve E (maximum comfortable threshold curve).

In operation, a software program can be used to automate any parts of the method from Steps 1A, 1B, Step 2, Step 3, and Steps 4A, 4B. In particular, Steps 2, 3 and 4A, are amenable to being implemented with a software program. Once a calibration curve has been generated in accordance with Step 1A or Step 1B, or a combination of both steps, various stimuli having parameter pairs (pulsewidth, amplitude) may be presented to the patient, in accordance with the calibration curve A. With respect to Step 2 and Step 3, the stimulus may begin with presentation of the lowest value parameter pair (pulsewidth, amplitude) of the calibration curve and increased incrementally until the patient reports a just noticeable perceived effect from the stimulation. This provides the threshold stimulus (P1, A1) parameters. The patient can report when the stimulus is a threshold (just noticeable) by conveying to the software program, e.g., pressing a key, whereby the software program can record into a database the specific stimulus parameters (P1, A1). Alternatively, the patient can indicate an effect perceived by indicating it vocally to a software operator, who can then take action to record the specific stimulus parameter (P1, A1), for example, into a memory storage. The patient can say "stop" or provide some other vocal signal indicating that a sensation has been felt.

In another embodiment of the method of the present invention, instead of using patient perception as proxies for nerve capture, other forms of feedback signal may be used to indicate when nerve fibers are being captured (stimulated). For example, signals that derive from the physiological response to the stimulation can be used, including an evoked potential measured with recording electrodes, the evoked potential having a defined morphology, amplitude or peak latency. Such recording electrodes may be placed on various parts of the body such as over or in the brain, in the spinal column, in the periphery or near or on the heart. Other transducible signals can include a signal from an accelerometer placed on a body part that is affected by the stimulation, a signal from an optical or electrical plethysmograph placed on a body part, which can detect a change resulting from the nerve stimulation. Such signals can be instantaneously captured and analyzed using a microprocessor in an external device or placed within an implantable stimulator. When a body effect is sensed by a sensing device, a tone may be provided to indicate to the patient or to a third person that nerve fibers are being captured by a particular stimulus.

With respect to Step 4A, box 104, after P1 has been determined in Step 3, box 103, it is necessary to find the maximum comfortable amplitude A2. The software program can hold P1 constant while varying the stimulus amplitude in incremental steps beginning, for example, from A1.

A further embodiment of the present method determines the maximum comfortable threshold amplitude, A2, without first determining the perception threshold, A1. In such a procedure the calibration curve A is used to immediately determine the maximum comfortable threshold defined by a pulsewidth and amplitude. In operation, various stimuli with parameter pairs (pulsewidth, amplitude) located on the predetermined calibration curve are presented to the patient, for example, in increasing fashion. Using feedback from the patient, or some other means, the maximum comfortable threshold is determined. Once a satisfactory maximum comfortable threshold stimulus is reached, no further adjustments are performed. However, if no sets of parameters (pulsewidth, amplitude) of the predetermined calibration curve provides adequate stimulation, a different calibration curve must be programmed employing larger pulsewidths. The method of generating the predetermined calibration curve already discussed are applicable to this embodiment.

While the invention herein disclosed has been described by means of specific embodiments and applications thereof, numerous modifications and variations could be made thereto by those skilled in the art without departing from the scope of the invention set forth in the claims.

What is claimed is:

1. A method of determining an optimal therapeutic stimulus (pulsewidth, amplitude), for stimulating nerve with at least one electrode (17), the method comprising:
    (a) providing a predetermined calibration curve defined by sets of paired parameter values (pulsewidth, amplitude);
    (b) determining an optimal pulsewidth value, P1, by presenting sets of paired parameter values (pulsewidth, amplitude) that are part of the calibration curve, until a threshold stimulus parameter pair (P1, A1) is found which elicits a threshold or a just noticeable response in a patient; and
    (c) determining an maximum comfortable amplitude value, A2, by holding constant the pulsewidth, P1, found in the preceding step.

2. The method of claim 1, wherein the threshold stimulus (P1, A1) is measured by a sensing instrument.

3. The method of claim 2, wherein the sensing instrument is selected from the group consisting of a plethysmograph, an accelerometer and a transducer for detecting evoked potentials.

4. The method of claim 1, further comprising:
    (d) determining the therapeutic value, A3, by holding pulsewidth, P1, found in step (b) constant, and setting A3 equal to A2,
    wherein step (c) is accomplished by incrementally increasing stimulus amplitude until the maximum comfortable threshold amplitude, A2, is found, while holding the pulsewidth, P1, found in step (b) constant.

5. The method of claim 1, further comprising:
    (d) determining the therapeutic value, A3, by holding pulsewidth, P1, found in step (b) constant, and setting A3 value less than A2,
    wherein step (c) is accomplished by incrementally increasing stimulus amplitude until the maximum comfortable threshold amplitude, A2, is found, while holding the pulsewidth, P1, found in step (b) constant.

6. The method of claim 1, wherein the calibration curve has an elbow occurring at a pulsewidth value of between about 100 to 300 microseconds.

7. The method of claim 1, wherein step (c) for determining A2 is accomplished by multiplying the amplitude A1 found in step (b) by a multiplicative factor.

8. The method of claim 7, wherein the multiplicative factor is about 1.4.

9. The method of claim 1, wherein the calibration curve is derived based on pre-measurement of maximum electrode impedance setting and ensuring that maximum comfortable threshold voltage is well below system compliance voltage.

10. The method of claim 1, wherein the calibration curve is derived based on minimizing current drain, in accordance with the relation:

$$P_{drain} = \{(I_{stim} * \text{Pulsewidth}_{stim} * \text{Rate}_{stim})^2 * Z_{combination}\} + P_{sys}.$$

11. The method of claim 1, wherein the calibration curve provides a UR that is sufficiently wide to provide stimulation to yield both a perception threshold and a maximum comfortable threshold.

12. The method of claim 1, wherein the step (b) of determining (P1, A1) is performed using a software program to present the various parameter values (pulsewidth, amplitude) in accordance with the predetermined calibration curve.

13. The method of claim 1, wherein the at least one electrode (17) chosen presents the highest impedance among possible available electrodes.

14. A method of determining optimal stimulus pulsewidth and amplitude for stimulating nerves with at least one electrode (17), the method comprising:
(a) providing a predetermined calibration curve comprising a set of pulsewidth (70) and amplitude values; and
(b) selecting a stimulus pulsewidth (70) and an amplitude which provides a maximum comfortable threshold by delivering stimuli to the at least one electrode (17), the stimuli chosen from pulsewidth and amplitude parameter pairs which are part of the calibration curve.

15. The method of claim 14, wherein the calibration curve is derived based on pre-measurement of maximum electrode impedance setting and ensuring that the maximum threshold is well below the system compliance voltage.

16. The method of claim 14, wherein the calibration curve is derived based on minimizing current drain, in accordance with the relation:

$$P_{drain} = \{(I_{stim} * \text{Pulsewidth}_{stim} * \text{Rate}_{stim})^2 * Z_{combination}\} + P_{sys}.$$

17. The method of claim 14, wherein the calibration curve provides a UR that is sufficiently wide to provide stimulation to yield both a perception threshold and a maximum threshold.

18. The method of claim 14, wherein the at least one electrode (17) chosen presents the highest impedance among possible available electrodes.

19. The method of claim 14, wherein in step (b) delivering stimuli to the at least one electrode (17), stimuli chosen from pulsewidth and amplitude parameter pairs which are part of the calibration curve is performed by using a software program.

* * * * *